US00PP31759P2

(12) United States Plant Patent
Welzel

(10) Patent No.: US PP31,759 P2
(45) Date of Patent: May 12, 2020

(54) POINSETTIA PLANT NAMED 'WEL19375'

(50) Latin Name: *Euphorbia pulcherrima*
Varietal Denomination: WEL19375

(71) Applicant: Christian Welzel, Kerken (DE)

(72) Inventor: Christian Welzel, Kerken (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,254

(22) Filed: Mar. 12, 2019

(51) Int. Cl.
*A01H 5/02* (2018.01)
*A01H 6/38* (2018.01)

(52) U.S. Cl.
USPC ..... Plt./303

(58) Field of Classification Search
USPC ..... Plt./303, 307
CPC ..... A01H 5/02; A01H 5/0244; A01H 5/00; A01H 6/38; A01H 6/385
See application file for complete search history.

(56) References Cited

U.S. PATENT DOCUMENTS

PP13,721 P3 * 4/2003 Zerr ..... A01H 6/38 Plt./303

* cited by examiner

*Primary Examiner* — June Hwu
(74) *Attorney, Agent, or Firm* — Barbara Campbell; James M. Weatherly; Cochran Freund & Young LLC

(57) ABSTRACT

A new poinsettia plant particularly distinguished by having red bracts with white spots and very good keeping quality is disclosed.

1 Drawing Sheet

Genus and species: *Euphorbia pulcherrima.*
Variety denomination: 'WEL19375'.

CROSS REFERENCE TO RELATED APPLICATION

An application for Community Plant Variety Rights for the instant variety was filed on Nov. 22, 2018, and has application number 2018/3063, the entire contents of which are incorporated herein by reference.

BACKGROUND OF THE NEW PLANT

The present invention comprises a new and distinct variety of poinsettia, botanically known as *Euphorbia pulcherrima* and hereinafter referred to by the variety name 'WEL19375'. 'WEL19375' was derived from a naturally occurring mutation of an unknown variety within a proprietary stock of a range of varieties in a greenhouse in Kerken, Germany.

In November 2015, a single plant was selected in Kerken, Germany. In December 2015, 'WEL19375' was first asexually propagated by vegetative apical cuttings. 'WEL19375' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Red bracts with white spots; and
2. Very good keeping quality.

DESCRIPTION OF THE PHOTOGRAPH

This new poinsettia plant is illustrated by the accompanying photograph which shows an overall view of the whole plant. The photograph is of a plant approximately 10 weeks old grown indoors in Stuttgart, Germany in November 2018. The colors shown are as true as can be reasonably obtained by conventional photographic procedures.

DESCRIPTION OF THE NEW VARIETY

The following detailed descriptions set forth the distinctive characteristics of 'WEL19375'. The data which define these characteristics were collected from asexual reproductions carried out in Stuttgart, Germany. Data was collected on plants aged approximately 20 weeks-old after potting and grown in a glass greenhouse in Stuttgart, Germany in December 2018. Color references are to The R.H.S. Colour Chart of The Royal Horticultural Society of London (R.H.S.), 5$^{th}$ edition (2007) unless where otherwise stated.

Classification:
- *Family.*—Euphorbiaceae.
- *Species.*—*Euphorbia pulcherrima.*
- *Common name.*—Poinsettia.
- *Variety.*—'WEL19375'.

Parentage: Mutation of proprietary unpatented, unnamed variety.

Growth:
- *Flowering response time.*—Approximately 56 days.
- *Keeping quality.*—Very good.

Plant description:
- *Form.*—Triangular.
- *Growth habit.*—Upright.
- *Height.*—23.0 cm to 25.0 cm.
- *Width.*—28.0 cm to 35.0 cm.
- *Average number of inflorescences per plant.*—5 to 6.

Propagation:
- *Type cuttings.*—Apical cuttings.
- *Time to produce a rooted cutting.*—4 weeks.

*Rooting habit and root color*.—Freely branching and white.

Lateral branches:

*Color*.—Lower quarter close to RHS N138B; upper three quarters close to RHS 59A.

*Length*.—20.0 cm to 22.0 cm.

*Internode length*.—1.5 cm to 4.0 cm.

*Diameter*.—0.5 cm to 0.8 cm.

*Branching habit*.—Freely branching.

*Number of lateral branches per plant*.—5 to 6.

*Texture*.—Smooth.

*Strength*.—Sturdy texture.

Leaves:

*Quantity*.—5 to 6 per lateral branch.

*Arrangement*.—Alternate.

*Transitional leaves*.—Few; lobing is weak, shape is ovate, length is 5 cm to 9 cm, width is 4 cm to 6 cm, the red part stays red (but paler) and the white spots stay green with the outer and more light-exposed parts are red and the remaining parts are green.

*Number of lobes on the leaf blade*.—0 to 3; more than 95% of the leaves have no lobes.

*Lobation depth*.—Shallow.

*Depth of the deepest sinus of the leaf blade*.—0.3 cm.

*Shape*.—Ovate.

*Apex*.—Acute.

*Base*.—Obtuse.

*Margin*.—Mostly entire.

*Length*.—7.0 cm to 12.0 cm.

*Width*.—5.0 cm to 7.0 cm.

*Texture (both surfaces)*.—Smooth.

*Vein color*.—Upper surface: Main vein (middle) is RHS 184A; secondary vein is RHS 184D and the tertiary vein is close to RHS N138B. Lower surface: Main vein (middle) is RHS 184A; secondary vein is RHS 184D and the tertiary vein is close to RHS N138B.

*Venation pattern*.—Reticulate.

*Variegation*.—Absent.

*Color*.—Mature foliage: Upper surface: Between RHS 139A and RHS N189A. Lower surface: Close to RHS N138B. Immature foliage: Upper surface: Close to RHS 139A. Lower surface: Close to RHS N138B.

*Leaf petiole*.—Length: 2.0 cm to 3.0 cm. Diameter: 0.2 cm to 0.3 cm. Color: Upper (part) surface: RHS 59A. Lower (part) surface: RHS 59A. Texture: Smooth. Strength: Medium.

Inflorescence:

*Type and habit*.—Cluster of cyathia.

*Quantity per lateral branch*.—1.

*Position relative to foliar plane*.—Above.

*Lastingness of inflorescence on the plant*.—4 weeks.

*Natural flowering season*.—End of November.

*Diameter*.—18.0 cm to 21.0 cm.

*Height*.—Approximately 3.0 cm.

*Fragrance*.—Absent.

Bracts:

*Number of bracts per inflorescence*.—12 to 16.

*Shape*.—Ovate.

*Apex*.—Acute.

*Base*.—Obtuse.

*Margin*.—Slightly serrate, young bracts mostly entire.

*Size*.—Length: 4.0 cm to 10.0 cm. Width: 3.0 cm to 7.0 cm.

*Texture (both upper and lower surfaces)*.—Smooth.

*Folding along the main vein*.—Absent.

*Twisting*.—Absent.

*Rugosity between the veins*.—Absent.

*Venation pattern*.—Reticulate.

*Vein color*.—Upper surface: RHS 184A. Lower surface: RHS 184A.

*Bract color, both surfaces*.—18-1760 (Barberry, the Pantone book of color published 1990) with irregular spots colored RHS NN155A; spot size is variable from small to medium size and variable in few to many for number of spots.

*Bract petiole*.—Length: 0.5 cm to 2.0 cm. Diameter: 0.2 cm to 0.3 cm. Color: Upper (part) surface: RHS 59A. Lower (part) surface: RHS 184A. Texture: Smooth. Strength: Medium.

Cyme:

*Diameter*.—1.5 cm to 3.0 cm.

*Cyathia number*.—7 to 8 per inflorescence.

*Deformation of glands of the cyathium*.—Absent.

*Timing of opening of cyathia*.—End of November. First pollen appears in parallel to opening of the nectar cups; stigmas appear 2 weeks later.

*Cyathium*.—Shape: Ovate. Texture (inner and outer surfaces): Smooth. Diameter: 0.4 cm to 0.6 cm. Length: 0.5 cm to 0.7 cm. Color: Lower part: RHS 141D. Upper part: 18-1760 (the Pantone book of color published 1990).

*Peduncle*.—Color: RHS 141D with reddish stripes close to RHS 184D. Length: 0.2 cm to 0.3 cm. Diameter: 0.1 cm to 0.15 cm. Texture: Smooth. Strength: Medium to strong.

*Nectar cups*.—Number: 1 per cyathium. Diameter: 0.1 cm. Length: 0.4 cm to 0.5 cm. Color: Close to RHS 28A. Shape: Lip-shaped. Texture (inner and outer surfaces): Smooth.

Reproductive organs:

*Stamen quantity*.—10 to 20 per cyathium.

*Stamen shape*.—Ovate.

*Filament length*.—0.2 cm.

*Filament color*.—18-1760 (the Pantone book of color published 1990).

*Pollen quantity*.—Moderate.

*Pollen color*.—Close to RHS 9C.

*Gynoecium*.—Not observed.

Fruit and seed set: None observed.

Disease and pest resistance: No special disease or pest resistance observed.

COMPARISON WITH PARENTAL AND COMMERCIAL LINE

A comparison between the instant plant and its mutation parent is not available. When 'WEL19375' is compared to the commercial line 'NPCW14221' (U.S. Plant Pat. No. 27,135), the following differences are noted in Table 1.

TABLE 1

| Characteristic | 'WEL19375' | 'NPCW14221' |
|---|---|---|
| Bract color | Rich, dark-red | Bright red |
| Stem color | Brownish-red | Green-red |
| Spots | Present | Absent |

I claim:

1. A new and distinct variety of poinsettia plant designated 'WEL19375' as illustrated and described herein.

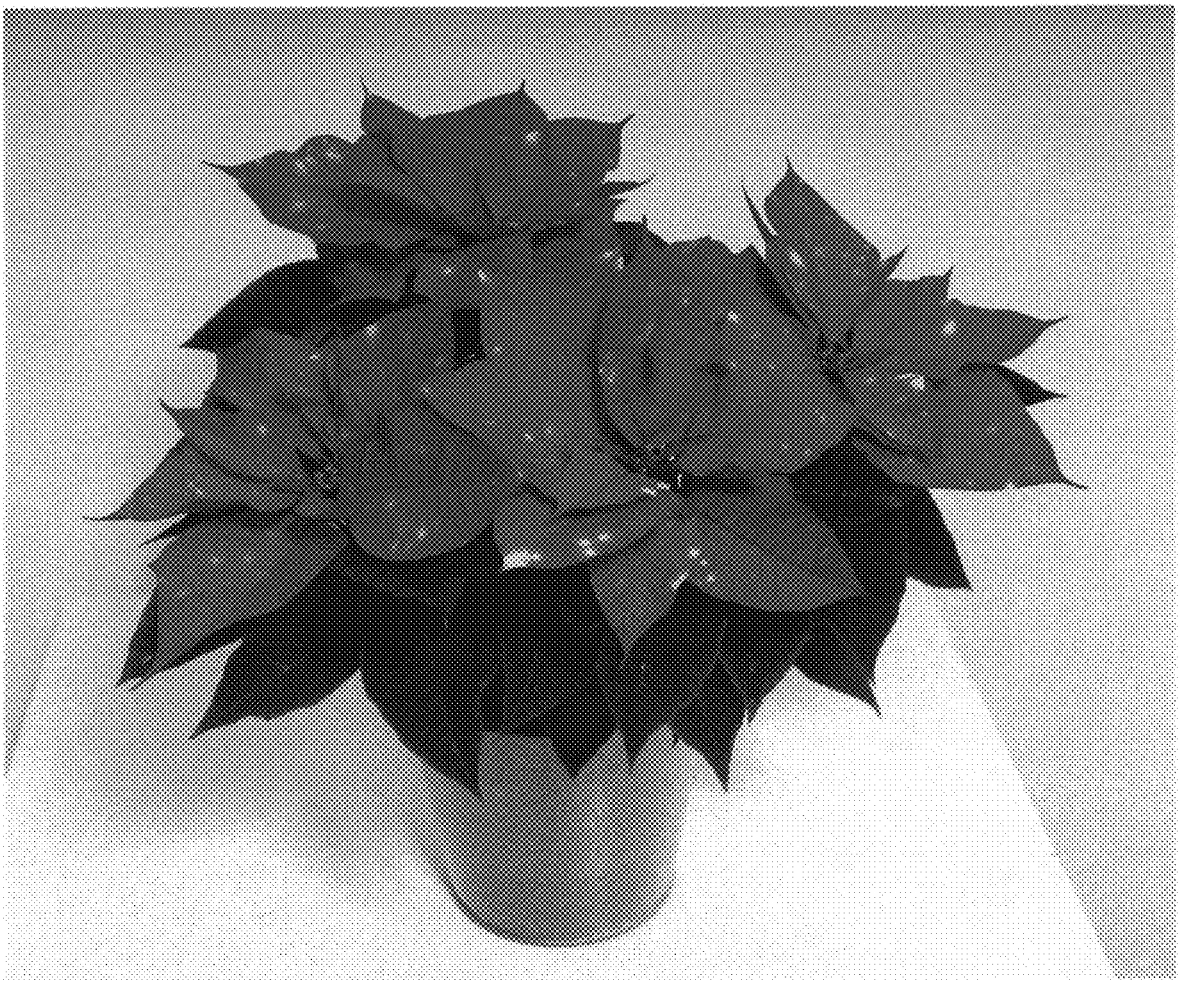

* * * * *